US008927772B2

(12) United States Patent
Watanabe et al.

(10) Patent No.: US 8,927,772 B2
(45) Date of Patent: Jan. 6, 2015

(54) TERTIARY AMINE PREPARATION PROCESS

(75) Inventors: Masahiko Watanabe, Sennan-gun (JP); Gosuke Tateno, Hannan (JP); Hirofumi Mizukoshi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/976,365

(22) PCT Filed: Dec. 27, 2011

(86) PCT No.: PCT/JP2011/080344
§ 371 (c)(1),
(2), (4) Date: Jun. 26, 2013

(87) PCT Pub. No.: WO2012/091071
PCT Pub. Date: Jul. 5, 2012

(65) Prior Publication Data
US 2013/0289309 A1 Oct. 31, 2013

(30) Foreign Application Priority Data

Dec. 27, 2010 (JP) ................................. 2010-291233
Dec. 27, 2011 (JP) ................................. 2011-286771

(51) Int. Cl.
C07C 209/16 (2006.01)
C01B 3/58 (2006.01)
(52) U.S. Cl.
CPC ............... *C07C 209/16* (2013.01); *C01B 3/586* (2013.01); *C01B 2203/0445* (2013.01); *C01B 2203/047* (2013.01)
USPC .......................................... 564/479; 564/480
(58) Field of Classification Search
None
See application file for complete search history.

(56) References Cited

U.S. PATENT DOCUMENTS

| 4,138,437 A | 2/1979 | Strauss et al. |
| 4,806,287 A | 2/1989 | Sulc et al. |
| 4,851,580 A | 7/1989 | Mueller et al. |
| 4,912,260 A | 3/1990 | Dobson et al. |
| 2005/0107637 A1 | 5/2005 | Gerlach et al. |
| 2005/0191224 A1 | 9/2005 | Endou |
| 2007/0149818 A1 | 6/2007 | Fukushima et al. |
| 2010/0029988 A1 | 2/2010 | Suzuki et al. |
| 2010/0168257 A1 | 7/2010 | Duisberg et al. |

FOREIGN PATENT DOCUMENTS

| EP | 0 729 785 A1 | 9/1996 |
| JP | 50-30804 | 3/1975 |
| JP | 52-19604 | 2/1977 |
| JP | 62-114940 A | 5/1987 |
| JP | 64-13060 A | 1/1989 |
| JP | 2-233 A | 1/1990 |
| JP | 2-234 A | 1/1990 |
| JP | 4-230246 A | 8/1992 |
| JP | 5-168930 A | 7/1993 |
| JP | 7-69999 A | 3/1995 |
| JP | 8-59566 A | 3/1996 |
| JP | 8-243392 A | 9/1996 |
| JP | 2001-151733 A | 6/2001 |
| JP | 2005-246116 A | 9/2005 |
| JP | 2005-527516 A | 9/2005 |
| JP | 2007-176889 A | 7/2007 |
| JP | 2007-176891 A | 7/2007 |
| JP | 2007-176892 A | 7/2007 |
| JP | 2008-150312 A | 7/2008 |
| JP | 2010-520807 A | 6/2010 |

OTHER PUBLICATIONS

International search report issued in PCT/JP2011/080344 mailed Mar. 27, 2012.

*Primary Examiner* — Brian J Davis
(74) *Attorney, Agent, or Firm* — Birch, Stewart, Kolasch & Birch, LLP

(57) ABSTRACT

The present invention relates to a process for producing a tertiary amine, including the following steps (1) and (2):
Step (1); introducing an alcohol having 1 to 36 carbon atoms and a raw amine represented by the following general formula (I) into a first reaction vessel to react with each other in the presence of a catalyst and hydrogen, and then continuing the reaction while discharging water produced in the reaction and a hydrogen-containing gas out of a reaction system in the first reaction vessel:

$$R^1R^2NH \quad (I)$$

wherein $R^1$ and $R^2$ are each independently a hydrogen atom or a hydrocarbon group having 1 to 36 carbon atoms; and
Step (2): introducing the hydrogen-containing gas discharged from the first reaction vessel into a second reaction vessel to reduce an amount of carbon monoxide contained in the hydrogen-containing gas, and then introducing a part or whole of the hydrogen-containing gas into the first reaction vessel.

19 Claims, No Drawings

TERTIARY AMINE PREPARATION PROCESS

FIELD OF THE INVENTION

The present invention relates to a process for producing tertiary amines, and more particularly, to a process for producing tertiary amines in which a hydrogen-containing gas by-produced in the reaction is recycled and reused to reduce an amount of hydrogen used therein.

BACKGROUND OF THE INVENTION

Tertiary amines are an important intermediate material in domestic and industrial application fields, and have been extensively used in various applications such as fabric softeners, shampoos, rinses, antistatic agents, detergents, dispersants, textile auxiliaries, etc.

There are known various processes for production of the tertiary amines. In one of these processes, an alcohol and an amine are contacted with each other in the presence of hydrogen and a catalyst. As the catalyst used in the above process, there are known transition metal catalysts such as copper-based catalysts (refer to Patent Document 1) and nickel-based catalysts (refer to Patent Document 2), noble metal catalysts such as ruthenium-based catalysts (refer to Patent Document 3) or the like.

In the production process using the above catalysts, the tertiary amines are produced through the following three steps (a) to (c).

Step (a): subjecting a raw alcohol to dehydrogenation reaction to produce an aldehyde;

Step (b): subjecting the thus produced aldehyde to nucleophilic addition reaction with an amine and then subjecting the obtained reaction product to dehydration reaction to produce an enamine; and Step (c): subjecting the thus produced enamine to hydrogenation reaction to produce the tertiary amine.

In the above production process, it is required that a large amount of a hydrogen gas is used as a substrate for the hydrogenation reaction or as a carrier gas for driving water produced in the reaction out of the reaction system, and further for the purposes of enhancing a reactivity and a selectivity and improving an appearance of the obtained reaction product or a coloring property when forming a derivative thereof.

Patent Document 1; JP 2-233A
Patent Document 2; JP 50-30804A
Patent Document 3; JP 8-243392A

SUMMARY OF THE INVENTION

In the process for producing the tertiary amines through the above steps (a) to (c), a large amount of a hydrogen gas is required and simultaneously a large amount of a hydrogen-containing gas is discharged. Therefore, from the viewpoint of environmental protection, it is desired to recycle and reuse the hydrogen-containing gas discharged. However, hitherto, the hydrogen-containing gas discharged has not been recycled or reused. In consequence, it has been attempted to use hydrogen contained in the hydrogen-containing gas again in the above process. As a result, it has been found that the above attempt to recycle and reuse the hydrogen-containing gas results in deteriorated yield of the tertiary amines as the aimed product.

The present invention relates to a process for producing a tertiary amine which is capable of reducing an amount of a hydrogen gas used in the reaction by recycling and reusing a hydrogen-containing gas discharged therefrom.

As a result of analyzing the hydrogen-containing gas discharged from the above production process, the present inventors have found that the hydrogen-containing gas contains carbon monoxide derived from the aldehyde produced in the step (a); the carbon monoxide acts as a catalytic poison; and the hydrogen-containing gas therefore becomes recyclable and reusable by removing the carbon monoxide therefrom.

Thus, the present invention relates to a process for producing a tertiary amine, including the following steps (1) and (2):

Step (1): introducing an alcohol having 1 to 36 carbon atoms and a raw amine represented by the following general formula (I) into a first reaction vessel to react with each other in the presence of a catalyst and hydrogen, and then continuing the reaction while discharging water produced in the reaction and a hydrogen-containing gas out of a reaction system in the first reaction vessel:

$$R^1R^2NH \tag{I}$$

wherein $R^1$ and $R^2$ are each independently a hydrogen atom or a linear, branched or cyclic, saturated or unsaturated hydrocarbon group having 1 to 36 carbon atoms with the proviso that $R^1$ and $R^2$ may be bonded to each other to form a saturated hydrocarbon ring or an unsaturated hydrocarbon ring; and Step (2): introducing the hydrogen-containing gas discharged from the first reaction vessel into a second reaction vessel to reduce an amount of carbon monoxide contained in the hydrogen-containing gas, and then introducing a part or whole of the hydrogen-containing gas into the first reaction vessel.

Effect of the Invention

According to the present invention, there is provided a process for producing a tertiary amine which is capable of reducing an amount of a hydrogen gas used in the reaction by recycling and reusing a hydrogen-containing gas discharged therefrom.

DETAILED DESCRIPTION OF THE INVENTION

The process for producing a tertiary amine according to the present invention includes a step (1) of introducing a specific alcohol and a raw amine represented by the above general formula (I) into a first reaction vessel to react with each other in the presence of a catalyst and hydrogen, and then continuing the reaction while discharging water produced in the reaction and a hydrogen-containing gas out of a reaction system in the first reaction vessel (hereinafter occasionally referred to as an "amination step"); and a step (2) of introducing the hydrogen-containing gas discharged from the first reaction vessel into a second reaction vessel to reduce an amount of carbon monoxide contained in the hydrogen-containing gas, and then introducing a part or whole of the hydrogen-containing gas into the first reaction vessel (hereinafter occasionally referred to as a "carbon monoxide reduction step").

In the followings, the respective components and the respective steps used in the present invention as well as the production apparatuses, etc., used for practicing the present invention are explained.

[Step (1); Amination Step]

In the amination step as the step (1) in the process of the present invention, the reaction proceeds as shown in the following reaction formula (II) to produce a tertiary amine as an aimed product.

$$R^1R^2NH + R^3OH \rightarrow R^1R^2NR^3 \qquad (II)$$

In the formula (II), $R^1$ and $R^2$ are each independently a hydrogen atom or a linear, branched or cyclic, saturated or unsaturated hydrocarbon group having 1 to 36 carbon atoms with the proviso that $R^1$ and $R^2$ may be bonded to each other to form a saturated hydrocarbon ring or an unsaturated hydrocarbon ring; and $R^3$ is a saturated or unsaturated hydrocarbon group having 1 to 36 carbon atoms.

In the above amination step, the alcohol ($R^3OH$) is subjected to dehydrogenation in the presence of a metal catalyst to produce an aldehyde, and then the resulting aldehyde is contacted with the raw amine to produce an enamine, and further hydrogen is added to the resulting enamine in the presence of the metal catalyst to produce the aimed tertiary amine.

In the above reaction, the aldehyde produced by dehydrogenation of the alcohol undergoes decarbonylation as a side reaction to thereby produce carbon monoxide. The thus produced carbon monoxide tends to act as a catalytic poison on the metal catalyst. Therefore, in the subsequent carbon monoxide reduction step as the step (2), an amount of carbon monoxide in the waste hydrogen is reduced.

The alcohol and the raw amine which may be used in the amination step are as follows.

<Alcohol>

The alcohol $R^3OH$ used in the present invention includes those alcohols containing a saturated or unsaturated hydrocarbon group having 1 to 36 carbon atoms.

The number of carbon atoms contained in the alcohol is preferably 2 or more, more preferably 6 or more, still more preferably 8 or more and further still more preferably 12 or more from the viewpoints of well-controlled pressure upon the reaction and easiness in handling of the resulting product. On the other hand, from the viewpoint of a good reactivity, the number of carbon atoms contained in the alcohol is preferably 30 or less, more preferably 24 or less, still more preferably 22 or less and further still more preferably 18 or less.

The alcohols having 1 to 36 carbon atoms are those alcohols containing a linear, branched or cyclic, saturated or unsaturated hydrocarbon group preferably having 2 to 30 carbon atoms, more preferably 6 to 24 carbon atoms, still more preferably 10 to 22 carbon atoms and further still more preferably 12 to 16 carbon atoms. In addition, the hydrocarbon group may contain one or more functional groups selected from a hydroxyl group, an amino group, an alkylamino group, an alkoxy group and the like.

Examples of the suitable alcohols include monohydric alcohols containing a saturated hydrocarbon group having 1 to 30 carbon atoms, dihydric alcohols containing a saturated hydrocarbon group having 1 to 30 carbon atoms and preferably 2 to 30 carbon atoms, saturated cyclic alcohols having 6 to 22 carbon atoms, and unsaturated cyclic alcohols having 6 to 22 carbon atoms.

Specific examples of the monohydric alcohols containing a saturated hydrocarbon group having 1 to 30 carbon atoms include methyl alcohol, ethyl alcohol, n-propyl alcohol, isopropyl alcohol, various butyl alcohols, various pentyl alcohols, various hexyl alcohols, various heptyl alcohols, various octyl alcohols, various nonyl alcohols, various decyl alcohols, various undecyl alcohols, various dodecyl alcohols, various tridecyl alcohols, various tetradecyl alcohols, 2-ethylhexyl alcohol, 3,5,5-trimethylhexyl alcohol, 3,7-dimethyloctyl alcohol and 2-propylheptyl alcohol. The term "various" as used herein means various kinds of isomers including "n-", "tert-" and "iso-" isomers.

Examples of the alcohols containing an unsaturated hydrocarbon group having 2 to 30 carbon atoms include oleyl alcohol and geraniol.

Specific examples of the dihydric alcohols containing a saturated hydrocarbon group having 2 to 30 carbon atoms include ethylene glycol, 1,2-propylene glycol, 1,3-propylene glycol, diglycol, 1,4-butanediol, 1,5-pentanediol, 1,6-hexanediol and 2,2-bis[4-hydroxycyclohexyl]propane.

Specific examples of the saturated cyclic alcohols having 6 to 22 carbon atoms include cyclopentanol, cyclohexanol, cyclopentyl methanol and cyclohexyl methanol.

Specific examples of the unsaturated cyclic alcohols having 6 to 22 carbon atoms include cyclopentenyl methanol, cyclohexenyl methanol and cyclohexenyl alcohol.

Examples of the other alcohols usable in the present invention include behenyl alcohol, icosyl alcohol, methoxyethanol, propoxyethanol, butoxyethanol, polyisobutyl alcohol, polypropyl alcohol, and Ziegler alcohols obtained by Ziegler method.

Among these alcohols, preferred are linear or branched alcohols having 2 to 30 carbon atoms, and more preferred are linear alcohols having 2 to 30 carbon atoms.

These alcohols may be used alone or in combination of any two or more thereof.

<Raw Amine>

The raw amine used in the present invention is an amine represented by the following general formula (I):

$$R^1R^2NH \qquad (I)$$

In the general formula (I), $R^1$ and $R^2$ are each independently a hydrogen atom or a linear, branched or cyclic, saturated or unsaturated hydrocarbon group having 1 to 36 carbon atoms. $R^1$ and $R^2$ may be bonded to each other to form a saturated hydrocarbon ring or an unsaturated hydrocarbon ring. In addition, the ring may also contain an unsaturated bond or a hetero atom (such as O, N and S). When $R^1$ and $R^2$ are a hydrocarbon group, the number of carbon atoms contained in the hydrocarbon group is preferably from 1 to 20, more preferably from 1 to 10, still more preferably from 1 to 6, further still more preferably from 1 to 5, further still more preferably from 1 to 4 and especially preferably from 1 to 3.

Examples of the suitable raw amine include aliphatic amines having 1 to carbon atoms, and aromatic amines having 6 to 20 carbon atoms. Meanwhile, ammonia may also be used as the raw amine.

Specific examples of the aliphatic amines having 1 to 20 carbon atoms include monoalkyl amines such as methyl amine, ethyl amine, n-propyl amine, isopropyl amine, various butyl amines, various pentyl amines and various hexyl amines; and dialkyl amines such as dimethyl amine, diethyl amine, di-n-propyl amine, diisopropyl amine, various dibutyl amines, various dipentyl amines and various dihexyl amines. Meanwhile, as the dialkyl amines, there may also be used those dialkyl amines containing two different kinds of alkyl chains which are different in number of carbon atoms from each other, such as methyl ethyl amine, methyl propyl amine, methyl butyl amine, methyl pentyl amine, methyl hexyl amine, methyl heptyl amine, methyl octyl amine, methyl dodecyl amine, methyl stearyl amine and ethyl propyl amine.

Specific examples of the aromatic amines having 6 to 20 carbon atoms include monoaryl amines such as phenyl amine, benzyl amine, methyl phenyl amine, ethyl phenyl amine, methyl benzyl amine and ethyl benzyl amine; diaryl amines such as diphenyl amine and dibenzyl amine; and analogous compounds thereof.

Examples of the other amines usable in the present invention include cyclic amines such as morpholine, pyrrolidine, piperazine and isoindoline; and analogous compounds thereof.

Meanwhile, the raw amine may be introduced into the first reaction vessel either continuously or intermittently. In addition, when using a liquid amine as the raw amine, a whole amount of the amine used in the reaction may be introduced at one time by a single operation.

<Catalyst Used in Amination Step>

Examples of the catalyst used in the amination step (amination catalyst) include transition metal catalysts such as copper-based catalysts and nickel-based catalysts, and noble metal catalysts such as ruthenium-based catalysts.

Specific examples of the copper-based catalysts include those catalysts described in JP 2-233A (catalysts composed of Cu, at least one transition metal selected from the group consisting of Cr, Mn, Fe, Ni, Co and Zn, a platinum group element and an alkali metal or alkali earth metal such as Li and Mg), those catalysts described in JP 2-234A (catalysts composed of Cu, a 4th period transition metal element such as Ni and Co, a platinum group element and a fourth component such as Al), and those catalysts described in JP 2001-151733A (catalysts composed of Cu, a 4th period transition metal and a platinum group element).

Specific examples of the nickel-based catalysts include those catalysts described in JP 50-30804A (catalysts composed of Ni, Cu and Cr), those catalysts described in JP 7-69999A (catalysts composed of Ni solely), those catalysts described in JP 2005-527516A (catalysts composed of Ni, Cu, Co and $ZrO_2$), and those catalysts described in JP 2007-176889A (catalysts composed of Ni, Cu and an alkali metal).

Specific examples of the ruthenium-based catalysts include those catalysts described in JP 8-243392A (catalysts composed of Ru and a porous oxide), those catalysts described in European Patent No. 729785 (catalysts composed of Ru and a noble metal), those catalysts described in JP 2008-150312A (catalysts composed of Ru, and a $ZrO_2$ composite oxide and/or $ZrO_2$ surface-treated with a metal), those catalysts described in JP 2007-176891A (catalysts composed of Ru and a porous oxide), those catalysts described in JP 2007-176892A (catalysts composed of Ru, at least one metal component selected from the group consisting of Ni and Co, and at least one metal component selected from the group consisting of La, Y, Mg and Ba), and those catalysts described in U.S. Pat. No. 4,912,260 (catalysts composed of Ru, Ni and at least one metal component selected from the group consisting of Pd, Re and Ir).

From the viewpoint of a good reactivity, the amination catalyst preferably contains, in addition to copper, at least one metal element selected from the group consisting of (i) a 4th period transition metal; (ii) platinum and a 5th period transition metal; and (iii) an alkali metal and an alkali earth metal, as main active components, and further satisfies the following conditions (a) to (c). Meanwhile, the respective ratios described in the following conditions (a) to (c) represent a molar ratio between metals.

(i) A 4th period transition metal: at least one metal element selected from the group consisting of nickel, cobalt, iron, chromium and zinc;

(ii) Platinum and a 5th period transition metal: at least one metal element selected from the group consisting of platinum, palladium, ruthenium and rhodium; and (iii) An alkali metal and an alkali earth metal: at least one metal element selected from the group consisting of lithium, sodium, potassium, rubidium, cesium, magnesium, calcium, strontium and barium.

copper/4th period transition metal=1/9 to 99/1, preferably 50/50 to 99/1;  Condition (a):

platinum and 5th period transition metal/(copper+4th period transition metal)=0 to 0.1, preferably 0 to 0.05; and  Condition (b):

4th period transition metal/(alkali metal+alkali earth metal)=1/0 to 1/2, preferably 1/0 to 1/1.  Condition (c):

Among the above amination catalysts, preferred are catalysts composed of copper and the 4th period transition metal (in particular, nickel), catalysts composed of copper, and platinum or the 5th period transition metal (in particular, ruthenium), and catalysts composed of copper, the 4th period transition metal (in particular, nickel) and the 5th period transition metal (in particular, ruthenium).

The amination catalysts may be used in the form of a supported catalyst prepared by supporting the above main active components on a porous carrier such as metal oxides and composite oxides. The shape of the supported catalyst is not particularly limited, and may be a powder shape, a spherical shape or a cylindrical shape (pellet-like shape).

These amination catalysts may be used alone or in combination of any two or more thereof.

The amination catalyst may be either a reduced catalyst or a non-reduced catalyst. From the viewpoints of good reactivity and selectivity, the amination catalyst is preferably in the form of a reduced catalyst. The reduced amination catalyst may be prepared by reducing the amination catalyst in a reducing atmosphere such as a hydrogen gas. Therefore, the reduced amination catalyst may also be prepared, for example, by conducting such a step in which the amination catalyst kept in an unreduced state is charged together with the raw alcohol into a reaction vessel, and then the contents of the reaction vessel are heated to the reaction temperature while introducing a hydrogen gas thereinto.

The amount of the amination catalyst used in the reaction is preferably appropriately controlled depending upon the reaction method used. When using a suspension bed batch method as the reaction method, from the viewpoints of good reactivity and selectivity, the amination catalyst is preferably used in an amount of from 0.01 to 30% by weight and more preferably from 0.1 to 10% by weight on the basis of the weight of the raw alcohol.

<Reaction Conditions of Amination Step>

The reaction method used in the amination step is not particularly limited, and may be either a suspension bed batch method or a fixed bed flowing method. The reaction temperature is preferably from 100 to 300° C. and more preferably from 150 to 250° C. from the viewpoint of a good reactivity. The reaction pressure is preferably from 100 kPa to 40 MPa and more preferably from 100 kPa to 25 MPa.

From the viewpoints of good reactivity and selectivity, when introducing hydrogen into the first reaction vessel, it is preferred that a mixed gas of hydrogen and a gas other than hydrogen be introduced into the reaction system. The gas to be mixed with hydrogen is not particularly limited, and any gas may be used as long as the gas thus mixed with hydrogen gives no adverse influence on hydrogen and the amination reaction. By using the mixed gas, it is possible to effectively remove water produced in the reaction out of the reaction system.

The velocity of the hydrogen-containing gas introduced into the first reaction vessel is preferably from 3 to 300 NL/h, more preferably from 8 to 100 NL/h and still more preferably from 20 to 50 NL/h per 1 kg of the raw alcohol. The "NL" in the above unit as used herein means a volume (normal liter) under a normal condition, i.e., as measured at 0° C. under a pressure of 101.3 kPa.

The water produced in the reaction may be removed from the reaction system either intermittently or continuously. From the viewpoint of good reactivity and selectivity, the water is preferably continuously removed from the reaction system. The water produced in the reaction may also be removed from the reaction system by previously adding an adequate solvent to the reaction system and then subjecting the water to azeotropic distillation therewith.

The hydrogen-containing gas thus discharged from the first reaction vessel may be stored in a tank, etc., and then introduced into the second reaction vessel, or may be directly introduced as such into the second reaction vessel without being stored in a tank, etc.

Meanwhile, in the case where a gaseous amine is used as the raw amine, from the viewpoints of ensuring a good reactivity in the second reaction vessel and suppressing occurrence of undesirable side reactions therein, it is preferred to previously remove the amine gas remaining in the hydrogen gas prior to introduction thereof into the second reaction vessel. The residual amine gas may be removed using an acid scrubber or the like (the below-mentioned step (A)).

The term "gaseous" as used herein means that the gas has a vapor pressure of 1 kPa or more as measured at a normal temperature (25° C.).

[Step (2): Carbon Monoxide Reduction Step]

In the above amination step, a part of the aldehyde produced undergoes a side reaction (decarbonylation reaction) and is converted into carbon monoxide. The thus produced carbon monoxide tends to cause problems such as covering of active sites on the amination catalyst used in the amination step and formation of a composite material with the amination catalyst to thereby deactivate the catalyst. Therefore, in the present invention, in order to recycle and reuse the hydrogen-containing gas, it is necessary to reduce an amount (concentration) of the carbon monoxide contained in the hydrogen-containing gas in the second reaction vessel.

As the method of reducing an amount of the carbon monoxide contained in the hydrogen-containing gas, there may be used (i) a method in which the carbon monoxide is adsorbed with an adsorbent material such as activated carbon; (ii) a biochemical method in which the carbon monoxide is adsorbed in hemoglobin or the like; (iii) a chemical method in which the carbon monoxide is further oxidized and converted into carbon dioxide; (iv) a methanation method in which the carbon monoxide is converted into methane; and the like.

Among these methods, from the industrial viewpoints, preferred is the method (iv) in which the carbon monoxide is converted into methane using a catalyst (methanation method).

Meanwhile, when using the alcohol having 6 to 36 carbon atoms and the raw amine of the above general formula (I) in which $R^1$ or $R^2$ has 1 to 6 carbon atoms, the catalyst tends to be more readily deactivated by the carbon monoxide. Therefore, if the above alcohol and raw amine are used to produce the aimed tertiary amine, the following step (3) is preferably further provided.

<Catalyst Used in Carbon Monoxide Reduction Step>

Examples of the catalyst used in the methanation method include nickel, cobalt, ruthenium, platinum, rhodium, palladium, molybdenum, tungsten and rhenium. In the present invention, among these catalysts, nickel, cobalt and ruthenium which exhibit a higher catalytic activity are especially preferably used.

Meanwhile, in the catalyst, one or more metals among the above metals may be used as main active components, and the other metals different from the main active components may be used as auxiliary active components.

In addition, the above main active components may be supported on a porous carrier formed of a metal oxide such as $Al_2O_3$, $SiO_2$, $TiO_2$, $CeO_2$, $MgO$ and $La_2O_3$ or a composite oxide thereof from the viewpoint of enhancing a catalytic activity thereof. Further, from the viewpoints of high catalytic activity and good availability, there may be used commercially available catalysts such as $Ru/\gamma$-$Al_2O_3$ and Ni/diatomaceous earth.

The shape of the methanation catalyst is not particularly limited, and may be any of a powder shape, a spherical shape and a cylindrical shape (pellet-like shape).

<Reaction Conditions of Carbon Monoxide Reduction Step>

The reaction temperature used in the carbon monoxide reduction step is preferably controlled to vary according to the catalyst used therein from the viewpoint of a good reactivity.

When using at least one metal selected from the group consisting of ruthenium, platinum, rhodium, palladium, tungsten and rhenium as a main active component of the catalyst, the reaction temperature is preferably from 100 to 350° C. and more preferably from 120 to 300° C.

When using at least one metal selected from the group consisting of nickel, cobalt and molybdenum as a main active component of the catalyst, the reaction temperature is preferably from 150 to 600° C. and more preferably from 200 to 550° C.

The reaction pressure in the carbon monoxide reduction step is preferably from 100 kPa to 40 MPa and more preferably from 100 kPa to 25 MPa even when using any of the above metals as a main active component of the catalyst.

The concentration of the carbon monoxide discharged from the second reaction vessel may vary depending upon the reaction conditions of the amination reaction in the first reaction vessel such as raw materials, catalysts, temperature and pressure used therein, the degree of quality of the aimed product as required, and the applications upon recycling and reusing, and is usually 5000 ppm or less, preferably 1000 ppm or less, more preferably 300 ppm or less, still more preferably 100 ppm or less and further still more preferably 20 ppm or less.

The hydrogen-containing gas discharged from the second reaction vessel may be stored in a tank, etc., and then introduced into the first reaction vessel and subjected to the amination reaction therein, or may be directly introduced into the first reaction vessel without being stored in a tank, etc., and continuously used therein. Alternatively, in the present invention, a part of the hydrogen-containing gas discharged from the second reaction vessel may be introduced into a reaction vessel other than the first reaction vessel and the second reaction vessel to recycle and reuse hydrogen contained therein.

Meanwhile, when the hydrogen-containing gas is circulated between the first reaction vessel and the second reaction vessel, a gas holder having an adequate capacity is preferably provided on a flow path between the first reaction vessel and the second reaction vessel in order to suitably control a pressure in the flow path.

[Step (3): Hydrogen Treatment Step]

When continuously conducting the treatment for reducing the amount (concentration) of carbon monoxide in the second reaction vessel (carbon monoxide reduction step), the metal catalyst used in the second reaction vessel tends to be deteriorated in catalytic activity with time. Therefore, in the present invention, it is preferred to provide a hydrogen treatment step in which the metal catalyst used in the second reaction vessel is treated with hydrogen to regenerate a catalytic activity of the catalyst.

As the method of treating the metal catalyst with hydrogen, there may be used the method of flowing a hydrogen gas through the second reaction vessel. When regenerating the catalyst by this method, the amount of hydrogen flowing through the second reaction vessel is preferably from 300 to 30000 NL/h, more preferably from 1000 to 10000 NL/h and still more preferably from 2000 to 5000 NL/h per 1 kg of the metal catalyst (methanation catalyst) from the viewpoint of efficiently treating the metal catalyst therewith. The temperature and pressure used in the hydrogen treatment step may be in the same ranges as used in the carbon monoxide reduction step.

Also, the hydrogen treatment step is preferably carried out for a period of from 0.3 to 3 h while flowing hydrogen at the above-specified flow rate.

[Step (A)]

In the present invention, in addition, the step (A) for reducing an amount of the amine contained in the hydrogen-containing gas discharged from the first reaction vessel is preferably provided between the step (1) and the step (2). More specifically, the means for removing the residual amine gas from the hydrogen-containing gas is preferably provided between the first reaction vessel and the second reaction vessel in order to prevent the gaseous amine from entering in the second reaction vessel.

In the present invention, the hydrogen-containing gas discharged in the step (1) is preferably contacted with water to reduce an amount of the raw amine contained in the hydrogen-containing gas. The hydrogen-containing gas is more preferably contacted with an acid aqueous solution to reduce an amount of the raw amine contained in the hydrogen-containing gas.

As the method of contacting the hydrogen-containing gas with water or the acid aqueous solution, there may be used a method of bubbling the hydrogen-containing gas in water or the acid aqueous solution to absorb the amine in water or the acid aqueous solution, or a method of bringing the hydrogen-containing gas into counter-flow contact with water or the acid aqueous solution while showering water or the acid aqueous solution.

As the specific means for removing the amine, there may be used an absorption tower using water as a solvent, an acid scrubber using a sulfuric acid aqueous solution as an absorbing medium, or the like. In such a means, it is preferred that the hydrogen-containing gas is first absorbed in an absorbing medium such as water to recover most of the amine therein, and then the residual amine is further removed by the acid scrubber.

Meanwhile, an alkali scrubber may also be provided in order to neutralize the solution scattered by a flow of the hydrogen-containing gas after being treated through the acid scrubber, etc.

The concentration of the residual amine contained in the hydrogen-containing gas obtained though the step (A) is preferably 1% by weight or less, more preferably 0.2% by weight or less and still more preferably 0.05% by weight or less.

[Production Apparatus]

The production apparatus for practicing the present invention is not particularly limited, and any suitable apparatuses can be used as long as they are capable of carrying out the above amination step and carbon monoxide reduction step. For example, there may be used an apparatus including a first reaction vessel in which an amination reaction is conducted, a second reaction vessel in which carbon monoxide contained in a hydrogen-containing gas discharged from the first reaction vessel is removed, and a conduit or pipe directly or indirectly connecting the first reaction vessel and the second reaction vessel with each other.

The first reaction vessel is preferably equipped with inlet tubes for introducing hydrogen and the raw amine thereinto, and further fitted with a condenser and a separator for condensing and separating water produced in the reaction, hydrogen gas, alcohol, etc.

The second reaction vessel is preferably a reactor capable of conducting the above methanation reaction therein, and may also be only a reactor capable of conducting removal or conversion of carbon monoxide.

Between the first reaction vessel and the second reaction vessel, there is preferably provided the above means for removing an excess amount of the amine which has been unconsumed in the amination reaction.

An outline of one preferred embodiment of the present invention is explained below by referring to a batch-type reaction as an example thereof.

First, the alcohol as a raw material and the catalyst are charged into an amination reaction vessel as the first reaction vessel, and then hydrogen is introduced thereinto. Then, heating of the contents in the first reaction vessel is initiated while sufficiently stirring. The catalyst is reduced during the heating and thereby activated. After reaching the predetermined temperature, the raw amine is introduced into the first reaction vessel to initiate the amination reaction. The raw amine may be introduced into the first reaction vessel either continuously or intermittently. When using a liquid amine as the raw amine, the liquid amine may be introduced at one time. Water produced during the reaction is discharged out of the reaction system together with a waste hydrogen gas (a mixed gas of hydrogen and unreacted gaseous amine in the case of using the gaseous amine) and a small amount of oil components such as alcohol and hydrocarbons, and fed through a condenser and a separator to separate the water from the oil components. The thus separated oil components may be fed back to the first reaction vessel.

The hydrogen-containing gas discharged from the first reaction vessel was introduced into the second reaction vessel. When using a gaseous amine as the raw amine, the hydrogen-containing gas contains the unreacted gaseous amine. Therefore, it is preferred that the hydrogen-containing gas is allowed to flow through an amine gas removal means to remove the amine gas therefrom, and then introduced into the second reaction vessel. The hydrogen-containing gas discharged from the second reaction vessel is fed again back to the amination reaction vessel and reused therein.

As described above, the present invention relates to:

[1] A process for producing a tertiary amine which includes the following steps (1) and (2):

Step (1): introducing an alcohol having 1 to 36 carbon atoms and an amine represented by the following general formula (I) into a first reaction vessel to react with each other in the presence of a catalyst and hydrogen, and then continuing the reaction while discharging water produced in the reaction and a hydrogen-containing gas out of a reaction system in the first reaction vessel:

$$R^1R^2NH \qquad (I)$$

wherein $R^1$ and $R^2$ are each independently a hydrogen atom or a linear, branched or cyclic, saturated or unsaturated hydrocarbon group having 1 to 36 carbon atoms with the proviso that $R^1$ and $R^2$ may be bonded to each other to form a saturated hydrocarbon ring or an unsaturated hydrocarbon ring; and Step (2): introducing the hydrogen-containing gas discharged from the first reaction vessel into a second reaction vessel to reduce an amount of carbon monoxide contained in the hydrogen-containing gas, and then introducing a part or whole of the hydrogen-containing gas into the first reaction vessel.

The preferred embodiments of the present invention are as follows.

[2] The process for producing a tertiary amine as described in the above [1], wherein in the second reaction vessel, the hydrogen-containing gas introduced thereinto is contacted with a metal catalyst to reduce an amount of carbon monoxide contained in the hydrogen-containing gas.

[3] The process for producing a tertiary amine as described in the above [1] or [2], further including the following step (A) between the step (1) and the step (2):

Step (A): reducing an amount of the amine contained in the hydrogen-containing gas discharged from the first reaction vessel.

[4] The process for producing a tertiary amine as described in the above [3], wherein in the step (A), the hydrogen-containing gas is contacted with water to reduce an amount of the amine contained in the hydrogen-containing gas.

[5] The process for producing a tertiary amine as described in the above [3] or [4], wherein in the step (A), the hydrogen-containing gas is contacted with an acid aqueous solution to reduce an amount of the amine contained in the hydrogen-containing gas.

[6] The process for producing a tertiary amine as described in any one of the above [1] to [5], further including the following step (3):

Step (3): treating the metal catalyst used in the second reaction vessel with hydrogen.

[7] The process for producing a tertiary amine as described in any one of the above [2] to [6], wherein the metal catalyst used in the second reaction vessel contains at least one metal selected from the group consisting of nickel, cobalt, ruthenium, platinum, rhodium, palladium, molybdenum, tungsten and rhenium as a main active component.

[8] The process for producing a tertiary amine as described in the above [7], wherein the metal catalyst used in the second reaction vessel contains at least one metal selected from the group consisting of ruthenium, platinum, rhodium, palladium, tungsten and rhenium as a main active component, and the reaction in the second reaction vessel is carried out at a temperature of from 100 to 350° C. and preferably from 120 to 300° C.

[9] The process for producing a tertiary amine as described in the above [7], wherein the metal catalyst used in the second reaction vessel contains at least one metal selected from the group consisting of nickel, cobalt and molybdenum as a main active component, and the reaction in the second reaction vessel is carried out at a temperature of from 150 to 600° C. and preferably from 200 to 550° C.

[10] The process for producing a tertiary amine as described in any one of the above [2] to [9], wherein the reaction in the second reaction vessel is carried out under a pressure of from 100 kPa to 40 MPa and preferably from 100 kPa to 25 MPa.

[11] The process for producing a tertiary amine as described in any one of the above [1] to [10], wherein the reaction in the first reaction vessel is carried out at a temperature of from 100 to 300° C. and preferably from 150 to 200° C. under a pressure of from 100 kPa to 40 MPa and preferably from 100 kPa to 25 MPa.

[12] The process for producing a tertiary amine as described in any one of the above [1] to [11], wherein a velocity of the hydrogen-containing gas introduced into the first reaction vessel is preferably from 3 to 300 NL/h, more preferably from 8 to 100 NL/h and still more preferably from 20 to 50 NL/h per 1 kg of the raw alcohol.

[13] The process for producing a tertiary amine as described in any one of the above [6] to [12], wherein a velocity of the hydrogen gas introduced in the step (3) is preferably from 300 to 30000 NL/h, more preferably from 1000 to 10000 NL/h and still more preferably from 2000 to 5000 NL/h per 1 kg of the metal catalyst.

[14] The process for producing a tertiary amine as described in any one of the above [1] to [13], wherein the number of carbon atoms contained in the alcohol is 2 or more, preferably 6 or more, more preferably 8 or more, still more preferably 10 or more and further still more preferably 12 or more, and on the other hand, preferably 30 or less, more preferably 24 or less, still more preferably 22 or less and further still more preferably 18 or less.

[15] The process for producing a tertiary amine as described in any one of the above [1] to [14], wherein the number of carbon atoms contained in the raw amine is from 1 to 20, preferably from 1 to 10, more preferably from 1 to 6, still more preferably from 1 to 5 and further still more preferably from 1 to 3.

EXAMPLES

The present invention is described in more detail by referring to the following Examples. However, the following Examples are only illustrative and not intended to limit the invention thereto.

Example 1

Step (1): Amination Step

A 2 L separable flask as the first reaction vessel was fitted with a condenser and a separator for condensing and separating water produced in reactions, etc., and charged with a mixed alcohol (raw alcohol) containing lauryl alcohol (carbon number: 12) and myristyl alcohol (carbon number: 14) at a mass ratio (lauryl alcohol/myristyl alcohol) of 70/30 in a total amount of 1200 g.

A 1 L flask was charged with an aqueous solution prepared by dissolving copper nitrate, nickel nitrate and ruthenium chloride in water such that the molar ratio therebetween in terms of the respective metal atoms (Cu:Ni:Ru) is 4:1:0.01, and the aqueous solution was heated while stirring. When reaching a temperature of 50° C., zeolite was charged into the flask, and further when reaching a temperature of 90° C., a 10% by weight sodium carbonate aqueous solution was gradually dropped therein. The resulting mixture was aged for 1 h, and the obtained precipitate was separated by filtration, washed with water and then dried, and thereafter calcined at 600° C. for 3 h to thereby prepare a Cu—Ni—Ru/zeolite catalyst (molar ratio between the respective metal atoms: Cu:Ni:Ru=4:1:0.01). The thus prepared catalyst was added to the raw alcohol in the first reaction vessel in an amount of 0.14% by weight on the basis of the weight of the raw alcohol.

While stirring the resulting solution at 950 r/min, hydrogen was introduced into the flask at a flow rate of 36 NL/h using a circulating pump, and circulated through a series of reaction processes constructed from the first reaction vessel and the below-mentioned second reaction vessel. The contents of the first reaction vessel were heated to a temperature at which the catalyst was able to be reduced, and held at that temperature for a predetermined time to reduce the catalyst.

After completion of reduction of the catalyst, a mixture of dimethyl amine and a hydrogen gas was introduced into the reaction system. The reaction system was gradually heated to 225° C. and subjected to amination reaction while maintaining a temperature of 225° C. The reaction was appropriately monitored and traced by gas chromatography.

The hydrogen-containing gas discharged from the first reaction vessel was allowed to flow through an amine gas removal means (a means for removing an amine gas in which the hydrogen-containing gas introduced thereinto is passed through a flask filled with water while bubbling, and then passed through a sulfuric acid aqueous solution trap and a sodium hydroxide aqueous solution trap) to thereby remove the raw amine component contained in the hydrogen-containing gas. After the elapse of 30 min from initiation of the reaction, the concentration of the amine gas in the hydrogen-containing gas was measured by gas chromatography (chromatograph "GC-3200" (tradename) available from G. L. Sciences, Inc.; column: "Varian capillary column CP-SiL 8CB for Amines", 0.32 mm in inner diameter×50 m in length; film thickness: 5.0 μm; oven temperature: 60° C.; injection temperature: 110° C.; detector temperature: 110° C.; detector: TCD). As a result, it was confirmed that the concentration of the amine gas in the hydrogen-containing gas was below the detection limit (100 ppm or less). The hydrogen-containing gas from which the amine component was removed was introduced into the second reaction vessel through a 12 L waste gas holder made of SUS.

Meanwhile, an inside atmosphere of the waste gas holder was replaced with a pure hydrogen gas before initiation of the reaction, and the holder was operated under a pressure ranging from 103 to 160 kPa according to the degree of proceeding of the amination reaction.

Step (2); Carbon Monoxide Reduction Step

Nine (9.0) grams of a 0.5 wt % Ru/Al$_2$O$_3$ catalyst "Pellets, Type 146" (tradename) available from Johnson Matthey Corp., as a catalyst for the second reaction vessel were filled in an SUS reactor having an inner diameter of 1.1 cm. The temperature of the second reaction vessel was adjusted to 220° C., and the pressure of the second reaction vessel was adjusted to the same as that of the first reaction vessel. The hydrogen-containing gas discharged from the second reaction vessel was introduced into the first reaction vessel, and circulated therebetween to continue the reaction.

The time required until the amount of the unreacted alcohol remaining in the first reaction vessel was reduced to 1% by weight of an amount of the alcohol upon initiation of the reaction was regarded as the reaction time, and the amount of hydrogen used for the reaction time, the composition of the resulting reaction product, and the concentration of carbon monoxide contained in the hydrogen-containing gas when introduced into the first reaction vessel were respectively measured. The results are shown in Table 1.

Meanwhile, the concentration of carbon monoxide was repeatedly measured at intervals of 30 min from the time at which 30 minutes elapsed after initiation of the reaction up to the time of completion of the reaction using a gas chromatograph ("GC-14A" (tradename) available from Shimadzu Corp.; column: "Molecular Sieve 5A"; 3.2 mm in inner diameter×4 m in length; oven temperature: 80° C.; injection temperature: 80° C.; detector temperature: 80° C.; carrier: He gas, 60 mL/min) equipped with a methanizer ("MTN-1, Shimalite-Ni" (tradename) available from Shimadzu Corp.) to calculate an average value of the thus measured concentrations. In Example 1, all of the carbon monoxide concentrations thus measured were less than the detection limit (1 ppm).

Example 2

The reaction was carried out in the same manner as in Example 1 except that the temperature of the second reaction vessel was adjusted to 180° C., and the average concentration of carbon monoxide discharged from the second reaction vessel was maintained at 3700 ppm. The results are shown in Table 1.

Comparative Example 1

The reaction was carried out in the same manner as in. Example 1 except that the hydrogen-containing gas discharged from the first reaction vessel was discarded without being circulated, and a pure hydrogen gas was always introduced into the reaction system to conduct the reaction. The results are shown in Table 1.

Comparative Example 2

The reaction was carried out in the same manner as in Example 1 except that the hydrogen-containing gas discharged from the first reaction vessel was circulated back and introduced into the first reaction vessel without passing through the second reaction vessel. The results are shown in Table 1.

TABLE 1

| | | Composition of reaction product (wt %) | | | |
|---|---|---|---|---|---|
| | Reaction time (h) | Dimethyl alkyl amine | Mixture of dialkyl methyl amine and wax | Amount of hydrogen used (L) | Average concentration of carbon monoxide (ppm) |
| Example 1 | 4.6 | 95.7 | 3.3 | 21.5 | Less than detection limit |
| Example 2 | 5.0 | 93.6 | 5.3 | 21.0 | 3700 |
| Comparative Example 1 | 4.7 | 95.2 | 3.6 | 175.4 | — |
| Comparative Example 2 | 5.8 | 87.2 | 11.0 | 21.9 | 12900 |

From Table 1, it was confirmed that in the methods of Examples 1 and 2, since the amount of carbon monoxide by-produced was reduced, it was possible to recycle and reuse the hydrogen-containing gas by-produced, so that the amount of a hydrogen gas used in the reaction was considerably reduced.

On the other hand, when the hydrogen-containing gas was circulated back and introduced into the first reaction vessel without passing through the second reaction vessel and used in the reaction (Comparative Example 2), the concentration of carbon monoxide was increased, so that the amination catalyst was deteriorated in catalytic activity, resulting in decrease in yield of the aimed product.

Example 3

The reaction was carried out in the same manner as in Example 1 except that the raw alcohol was replaced with 1200 g of stearyl alcohol ("KALCOL 8098" (tradename) available from Kao Corp.). The results are shown in Table 2.

TABLE 2

| | Composition of reaction product (wt %) | | | |
|---|---|---|---|---|
| Reaction time (h) | Dimethyl alkyl amine | Mixture of dialkyl methyl amine and wax | Amount of hydrogen used (L) | Average concentration of carbon monoxide (ppm) |
| Example 3 4.2 | 94.3 | 3.9 | 27.2 | Less than detection limit |

The amount of hydrogen used in the reaction of Example 3 was 27.2 L. Assuming that the reaction was conducted without recovering hydrogen, an estimated amount of the hydrogen gas flowing through the reaction system was 151 L.

Example 4

The reaction was carried out in the same manner as in Example 1 except that the raw alcohol and the raw amine were replaced with decyl alcohol and monomethyl amine, respectively, and the reaction temperature, the concentration of the catalyst based on the raw alcohol and the hydrogen flow rate were changed to 195° C., 1.2% by weight and 18 NL/h, respectively. The results are shown in Table 3.

TABLE 3

| | Composition of reaction product (wt %) | | | |
|---|---|---|---|---|
| Reaction time (h) | Dialkyl methyl amine | Mixture of dimethyl alkyl amine, trialkyl amine and wax | Amount of hydrogen used (L) | Average concentration of carbon monoxide (ppm) |
| Example 4 4.1 | 94.7 | 1.6 | 24.1 | Less than detection limit |

The amount of hydrogen used in the reaction of Example 4 was 24.1 L. Assuming that the reaction was conducted without recovering hydrogen, an estimated amount of the hydrogen gas flowing through the reaction system was 74 L.

In addition, from the results of Examples 3 and 4, it was confirmed that according to the production process of the present invention, it was possible to produce various tertiary amines with a high yield and a high selectivity.

Example 5

The reaction was carried out in the same manner as in Example 1 except that the hydrogen-containing gas discharged from the first reaction vessel was directly introduced into the second reaction vessel without passing through the amine gas removal means. The amount of the amine component contained in the hydrogen-containing gas before introduced into the second reaction vessel was 1.0% by weight.

The results of Example 5 are shown together with the results of Example 1 and Comparative Example 2 in Table 4. From these results, it was confirmed that with the provision of the step (A), the production process was further enhanced in reactivity and selectivity to the dimethyl alkyl amine.

TABLE 4

| | | Composition of reaction product (wt %) | | | |
|---|---|---|---|---|---|
| | Reaction time (h) | Dimethyl alkyl amine | Mixture of dialkyl methyl amine and wax | Amount of hydrogen used (L) | Average concentration of carbon monoxide (ppm) |
| Example 1 | 4.6 | 95.7 | 3.3 | 21.5 | Less than detection limit |
| Example 5 | 5.9 | 88.2 | 7.5 | 26.7 | 2300 |
| Comparative Example 2 | 5.8 | 87.2 | 11.0 | 21.9 | 12900 |

Example 6

First Reaction

In order to reproduce the condition that the metal catalyst in the second reaction vessel was deteriorated, the steps (1) and (2) were carried out in the same manner as in Example 1 except that no amine gas removal means was provided between the first reaction vessel and the second reaction vessel, and the first reaction was terminated at the time at which the amount of the unreacted alcohol remaining in the first reaction vessel was reduced to 1% by weight of the amount of the alcohol upon initiation of the reaction. The concentration of the amine gas contained in the hydrogen-containing gas after the elapse of 30 min from initiation of the reaction was 1.0 ppm.

Step (3): Hydrogen Treatment Step

After completion of the first reaction, hydrogen was flowed through the second reaction vessel at 200° C. at a flow rate of 36 NL/h for 0.5 h to subject the metal catalyst used in the second reaction vessel to hydrogen treatment.

Second Reaction

Next, using the second reaction vessel in which the hydrogen treatment was conducted in the above previous step (3), the steps (1) and (2) were carried out under the same conditions as used in Example 1.

The time required until the amount of the unreacted alcohol remaining in the first reaction vessel was reduced to 1% by weight of an amount of the alcohol upon initiation of the reaction was regarded as the reaction time, and the amount of hydrogen used for the reaction time, the composition of the resulting reaction product, and the concentration of carbon monoxide contained in the hydrogen-containing gas when introduced into the first reaction vessel were respectively measured. The results are shown in Table 5.

Comparative Example 3

The same procedure as in Example 6 was repeated except that after completion of the first reaction, the metal catalyst in the second reaction vessel was subjected to no hydrogen treatment, namely the first reaction and the second reaction were successively conducted. The results are shown in Table 5.

TABLE 5

| | Reaction time (h) | Composition of reaction product (wt %) | | | Average concentration of carbon monoxide (ppm) |
| --- | --- | --- | --- | --- | --- |
| | | Dimethyl alkyl amine | Mixture of dialkyl methyl amine and wax | Amount of hydrogen used (L) | |
| Example 6 | 3.8 | 95.6 | 3.1 | 25.5 | Less than detection limit |
| Comparative Example 3 | 4.8 | 93.7 | 4.5 | 20.0 | 3100 |

In accordance with the present invention, since the metal catalyst in the second reaction vessel can be regenerated by subjecting the catalyst to the hydrogen treatment, it is possible to produce the tertiary amine with a high yield.

INDUSTRIAL APPLICABILITY

In the process for producing a tertiary amine according to the present invention, the amount of hydrogen used therein can be reduced, so that there can be provided a considerably ecological and clean industrial process for producing a tertiary amine which is capable of reducing a burden on environments.

The invention claimed is:

1. A process for producing a tertiary amine, comprising the following steps (1) and (2):
    Step (1): introducing an alcohol having 1 to 36 carbon atoms and an amine represented by the following general formula (I) into a first reaction vessel to react with each other in the presence of a catalyst and hydrogen, and then continuing the reaction while discharging water produced in the reaction and a hydrogen-containing gas out of a reaction system in the first reaction vessel:

$$R^1R^2NH \quad (I)$$

wherein $R^1$ and $R^2$ are each independently a hydrogen atom or a linear, branched or cyclic, saturated or unsaturated hydrocarbon group having 1 to 36 carbon atoms with the proviso that $R^1$ and $R^2$ may be bonded to each other to form a saturated hydrocarbon ring or an unsaturated hydrocarbon ring; and
    Step (2): introducing the hydrogen-containing gas discharged from the first reaction vessel into a second reaction vessel in which the hydrogen-containing gas is contacted with a metal catalyst to reduce an amount of carbon monoxide contained in the hydrogen-containing gas, and then introducing a part or whole of the hydrogen-containing gas into the first reaction vessel.

2. The process for producing a tertiary amine according to claim 1, further comprising the following step (A) between the step (1) and the step (2):
    Step (A): reducing an amount of the amine contained in the hydrogen-containing gas discharged from the first reaction vessel.

3. The process for producing a tertiary amine according to claim 2, wherein in the step (A), the hydrogen-containing gas is contacted with water to reduce an amount of the amine contained in the hydrogen-containing gas.

4. The process for producing a tertiary amine according to claim 2, wherein in the step (A), the hydrogen-containing gas is contacted with an acid aqueous solution to reduce an amount of the amine contained in the hydrogen-containing gas.

5. The process for producing a tertiary amine according to claim 1, further comprising the following step (3):
    Step (3): treating the metal catalyst used in the second reaction vessel with hydrogen to regenerate a catalytic activity of the metal catalyst.

6. The process for producing a tertiary amine according to claim 1, wherein the metal catalyst used in the second reaction vessel contains at least one metal selected from the group consisting of nickel, cobalt, ruthenium, platinum, rhodium, palladium, molybdenum, tungsten and rhenium as a main active component.

7. The process for producing a tertiary amine according to claim 6, wherein the metal catalyst used in the second reaction vessel contains at least one metal selected from the group consisting of ruthenium, platinum, rhodium, palladium, tungsten and rhenium as a main active component, and the reaction in the second reaction vessel is carried out at a temperature of from 100 to 350° C.

8. The process for producing a tertiary amine according to claim 6, wherein the metal catalyst used in the second reaction vessel contains at least one metal selected from the group consisting of nickel, cobalt and molybdenum as a main active component, and the reaction in the second reaction vessel is carried out at a temperature of from 150 to 600° C.

9. The process for producing a tertiary amine according to claim 1, wherein the reaction in the second reaction vessel is carried out under a pressure of from 100 kPa to 40 MPa.

10. The process for producing a tertiary amine according to claim 1, wherein the reaction in the first reaction vessel is carried out at a temperature of from 100 to 300° C. under a pressure of from 100 kPa to 40 MPa.

11. The process for producing a tertiary amine according to claim 1, wherein a velocity of the hydrogen-containing gas introduced into the first reaction vessel is from 3 to 300 NL/h per 1 kg of the raw alcohol.

12. The process for producing a tertiary amine as described in claim 5, wherein a velocity of the hydrogen gas introduced in the step (3) is from 300 to 30000 NL/h per 1 kg of the metal catalyst.

13. The process for producing a tertiary amine as described in claim 1, wherein the number of carbon atoms contained in the alcohol is 2 or more and 30 or less.

14. The process for producing a tertiary amine as described in claim 1, wherein $R^1$ and $R^2$ in the general formula (I) are each independently a hydrocarbon group having 1 to 20 carbon atoms.

15. The process for producing a tertiary amine as described in claim 1, wherein the metal catalyst used in the second reaction vessel contains at least one metal selected from the group consisting of ruthenium, platinum, rhodium, palladium, tungsten and rhenium as a main active component, and the reaction in the second reaction vessel is carried out at a temperature of from 120 to 300° C.

16. The process for producing a tertiary amine as described in claim 1, wherein the metal catalyst used in the second reaction vessel contains at least one metal selected from the group consisting of nickel, cobalt and molybdenum as a main active component, and the reaction in the second reaction vessel is carried out at a temperature of from 200 to 550° C.

17. The process for producing a tertiary amine as described in claim 1, wherein the reaction in the second reaction vessel is carried out under a pressure of from 100 kPa to 25 MPa.

18. The process for producing a tertiary amine as described in claim 1, wherein the reaction in the first reaction vessel is carried out at a temperature of from 100 to 300° C.

19. The process for producing a tertiary amine as described in claim 1, wherein the reaction in the first reaction vessel is carried out under a pressure of from 100 kPa to 40 MPa.

* * * * *